United States Patent
Passy et al.

(10) Patent No.: US 7,513,906 B2
(45) Date of Patent: Apr. 7, 2009

(54) PHOTOTHERAPY APPARATUS AND METHOD FOR BONE HEALING, BONE GROWTH STIMULATION, AND BONE CARTILAGE REGENERATION

(75) Inventors: Philip W. Passy, Clearwater, FL (US); Thomas A. D. Burgmann, Mississauga (CA); Ben G. Yacobi, Mississauga (CA)

(73) Assignee: MedX Health Corp. (CA)

( * ) Notice: Subject to any disclaimer, the term of this patent is extended or adjusted under 35 U.S.C. 154(b) by 0 days.

(21) Appl. No.: 11/141,989

(22) Filed: May 31, 2005

(65) Prior Publication Data

US 2006/0271131 A1 Nov. 30, 2006

(51) Int. Cl.
*A61N 5/06* (2006.01)

(52) U.S. Cl. .......................................... 607/88; 607/91

(58) Field of Classification Search ................. 128/898; 607/88–94; 600/410–415; 250/455.1
See application file for complete search history.

(56) References Cited

U.S. PATENT DOCUMENTS

| | | | | |
|---|---|---|---|---|
| 3,796,220 A | * | 3/1974 | Bredemeier | 606/18 |
| 4,686,992 A | * | 8/1987 | Dewey et al. | 606/4 |
| 4,974,114 A | * | 11/1990 | Kammerer | 361/159 |
| 6,063,108 A | * | 5/2000 | Salansky et al. | 607/89 |
| 6,443,978 B1 | * | 9/2002 | Zharov | 607/91 |
| 6,494,900 B1 | * | 12/2002 | Salansky et al. | 607/89 |
| 6,602,275 B1 | * | 8/2003 | Sullivan | 607/88 |
| 6,853,864 B2 | * | 2/2005 | Litovitz | 607/100 |
| 6,896,693 B2 | * | 5/2005 | Sullivan | 607/91 |
| 2003/0023283 A1 | * | 1/2003 | McDaniel | 607/88 |
| 2004/0191729 A1 | * | 9/2004 | Altshuler et al. | 433/215 |
| 2004/0193235 A1 | * | 9/2004 | Altshuler et al. | 607/88 |
| 2005/0163778 A1 | * | 7/2005 | Peritt et al. | 424/145.1 |

* cited by examiner

*Primary Examiner*—Ahmed M Farah
(74) *Attorney, Agent, or Firm*—Beyer Law Group LLP

(57) ABSTRACT

Phototherapy apparatus, incorporating interconnected radiation sources, such as diode laser cluster radiation devices, and method for bone healing, bone growth stimulation, and bone cartilage regeneration are disclosed. The method consists of applying the said radiation cluster apparatus conformally around the desired area of the bone to be treated and providing irradiation at appropriate wavelengths and power densities for a selected period of time to the said area of the bone structure to be treated. The apparatus incorporates a sufficient number of the diode laser cluster devices, or other appropriate light sources, which are adapted to be placed inside an appropriate brace (e.g., ankle brace or knee brace), or are embedded inside a reconfigurable foam, or are embedded inside deformable gel material, or are embedded within the cast, which facilitate radially-positioned sources for irradiation of the area to be treated.

26 Claims, 3 Drawing Sheets

PHOTOTHERAPY APPARATUS AND METHOD FOR BONE HEALING, BONE GROWTH STIMULATION, AND BONE CARTILAGE REGENERATION

FIELD OF THE INVENTION

The present invention relates generally to phototherapy and in particular to a phototherapy apparatus and method for bone healing, bone growth stimulation, and bone cartilage regeneration.

BACKGROUND OF THE INVENTION

The use of phototherapeutic treatment employing low-intensity irradiation has been widely demonstrated to offer benefits in the treatment of various physiological problems and dermatological conditions, such as, but not limited to, carpal tunnel syndrome, tendonitis, bone growth and regeneration, rheumatoid arthritis, wound healing, acne, and general pain control. Phototherapeutic treatment typically affects photoreceptors in the tissue, with consequent alterations in the biochemical processes of the cells. This is accompanied by an increase in local blood circulation and a strengthening of the immune defense system.

In the past several decades, it was also demonstrated that phototherapy is effective in promoting healing of bone, muscle, cartilage, tendon, and ligament. The mechanism in such treatments typically relates to the process of absorption of photons by mitochondria, followed by adenosine triphosphate (ATP) synthesis, which then influences the synthesis of such biological species as proteins, enzymes, DNA/RNA that are required for cell repair or regeneration and for promotion of cell proliferation.

Thus, to summarize briefly, it is widely accepted that absorbed light triggers biological changes within the body, and in such cases, the use of specific wavelengths of light accelerates cellular metabolic processes and stimulates vital chemical reactions. Specifically, phototherapy can (i) increase the circulation by promoting the formation of new capillaries, which accelerate the healing process, (ii) increase DNA/RNA synthesis, which assists damaged cells to be replaced more rapidly, (iii) stimulate collagen protein production, which is important for repairing damaged tissue and replacing old tissue, and (iv) stimulate the release of adenosine triphosphate (ATP) that is a major carrier of energy to cells.

It is important to note that the optical window of the skin, (i.e., a wavelength range with an optimal transmission of light) is in the range between about 600 nm and 1300 nm. Wavelengths, shorter or longer than that range are generally absorbed before reaching substantial depth.

In the case of bone growth and healing, the effect of low level laser therapy (LLLT) on bone regeneration relates to biostimulation of the tissues with monochromatic light. The LLLT has been shown to promote collagen production, accelerate cell proliferation, and enhance bone healing.

The various applications of phototherapy were outlined in various publications, some of which are listed in the References list (see, for example, *The science of low-power laser therapy* by Karui). It is thought that a low level optical radiation induces biostimulation related to photochemical and photophysical processes on the molecular and cellular levels.

The phototherapy efficacy is related to several major factors. These include spectral range, irradiance (i.e., power per surface area per wavelength), exposed surface area, choice of pulsing frequency, and exposure duration.

Typically, in phototherapy, a careful selection of the spectral content of light used for treatment is required. There were numerous studies confirming the importance of selecting a specific wavelength for phototherapy treatment to be optimal. For example, in the cases of treating wounds, such wavelengths include 680, 730 and 880 nm (Whelan, H. T. et al. J. Clin. Laser Med. Surg., vol. 19, No. 6, 305-314, 2001).

In recent years, numerous reports also clearly demonstrated the beneficial effects of laser phototherapy on bone regeneration and bone fractures. These effects are outlined by Tuner and Hode in "The Laser Therapy Handbook".

In the studies on bone regeneration, Pinheiro concluded that the use of LLLT at 830 nm substantially improved bone healing at early stages.

Ueda and Shimizu, in the paper entitled "Pulse irradiation of low-power laser stimulates bone nodule formation", demonstrated the effect of lower-power GaAlAs laser irradiation (830 nm, 500 mW) on acceleration of bone formation as a function of pulse frequency, and concluded that pulsed laser irradiation substantially stimulates bone formation and that pulse frequency is an important factor in bone formation.

De Souza Merli et al., in the paper entitled "Effect of Low-Intensity Laser Irradiation on the Process of Bone Repair", also showed that the use of low-intensity GaAlAs laser has beneficial effect on bone repair.

In relation to the foregoing discussion, note that visible, especially red and infrared light have been demonstrated to influence many changes at a cellular level. In general, the various tissue and cell types have their own specific light absorption characteristics. In other words, they absorb light at specific wavelengths only. For typically employed wavelength range of 600 to 900 nm, the radiation is absorbed closer to the surface for shorter wavelengths, whereas for longer wavelengths the penetration depth is greater.

In relation to providing therapy to such musculoskeletal system problems as nonunion fractures, spinal fusion, tendon injuries, and osteoporosis, in recent years, several bone stimulation methods for healing were developed (see for example a paper entitled "Enhancement of fracture healing with bone stimulators" by Anglen). Such bone stimulators for promotion of healing typically employ electromagnetic field or ultrasonic signal applied to the bone.

There are different types of electromagnetic field methods used for promoting healing of nonunion bone fractures (i.e., those that do not heal naturally). These include pulsed electromagnetic fields (PEMFs) and direct current methods. These therapy methods to promote healing of nonunion bone fractures were approved by the U.S. Food and Drug Administration (FDA).

Although the advantages of PEMF treatment are well established, in general, the potential hazards of overexposure to electromagnetic fields are widely debated and being explored by various regulatory governing bodies.

Various studies have indicated that electromagnetic fields may pose potential health hazards in such cases of patients as (i) those with cardiac pacemakers or other implanted electrical device, (ii) those with metallic clips and implants, (iii) those who received a localized cortisone injection in the past several weeks, and (iv) pregnant women.

Thus, in relation to the foregoing discussion, it is desirable to provide an apparatus and a method that do not produce such potential health hazards and have a capability of a relatively simpler and more economical means of therapy with fewer risks and harnnful effects, and therefore providing a safer alternative to electromagnetic field methods used in promoting healing of bone fractures.

It is therefore an object of the present invention to provide a novel phototherapy apparatus and method for stimulating bone growth and healing and bone cartilage regeneration.

SUMMARY OF THE INVENTION

Accordingly, in one aspect there is provided a phototherapy apparatus comprising:

a support adapted to overlie and conform generally to a region of a patient to be treated; and a plurality of radiation sources disposed on said support, each radiation source including at least one radiation emitting device to emit radiation to promote bone healing, bone growth stimulation and bone cartilage regeneration.

In one embodiment, each radiation source includes a plurality of radiation emitting devices. The radiation emitting devices are selected from the group consisting of laser diodes, light emitting diodes, thin-film electroluminescent devices, fiber-optic delivery systems and/or bandages incorporating nanocrystals that emit radiation at predetermined wavelengths in response to excitation. The radiation sources are arranged radially about the support. The radiation sources may be operated in one of a continuous and pulsed manner.

The radiation emitted by the radiation sources has a wavelength selected for the penetration of biological tissue and transmission to bone tissue. The support in one embodiment is a flexible brace adapted to surround and conform to the region of a patient to be treated. In another embodiment, the support is a cast or a deformable gel material. In this case, the radiation sources are embedded therein.

The phototherapy apparatus may further include a controller to control operation of the radiation sources to enable the radiation to be emitted in a desired pattern. A display may be provided to display phototherapy procedures and/or treatment protocols.

In another embodiment, the radiation emitting devices are accommodated by gimbal-type supports. In this manner, emitted radiation is collimated within a variable solid angle centered on the targeted area.

According to another aspect of the present invention there is provided a phototherapy method. A region of a patent to be treated is overlayed with the phototherapy apparatus described above. Irradiation at appropriate wavelengths and power densities is provided for a selected period of time to the area of the bone structure to be treated.

The radiation generated by the apparatus can be augmented with different types of electromagnetic field methods used for promoting healing of nonunion bone fractures.

BRIEF DESCRIPTION OF THE DRAWINGS

Embodiments will now be described by way of example only, with reference to the accompanying drawings, in which.

DETAILED DESCRIPTION OF THE EMBODIMENTS

Figure 1:
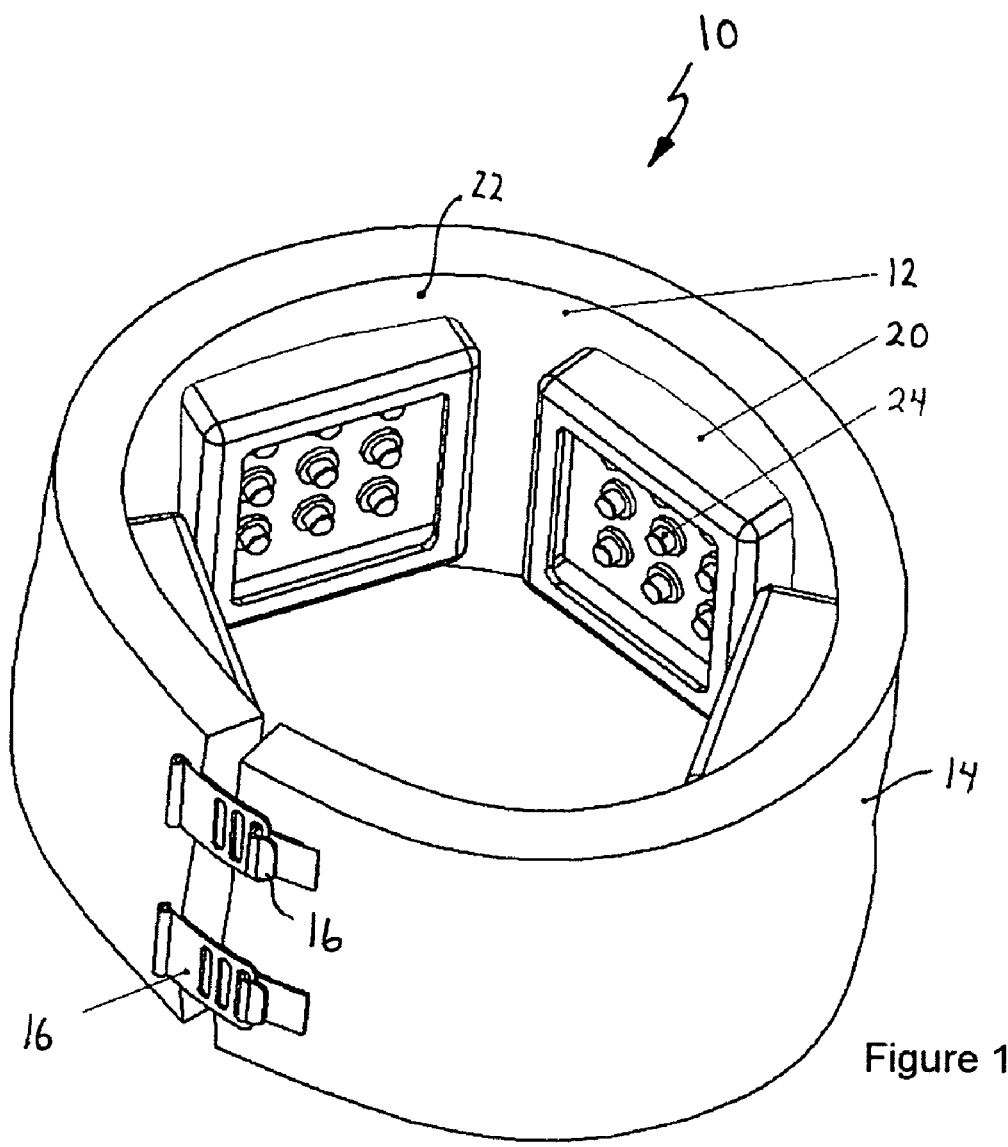
FIG. 1 is a schematic of a phototherapeutic apparatus for bone healing, bone growth stimulation, and bone cartilage regeneration.

Turning now to FIG. 1, a phototherapeutic apparatus for bone healing, bone growth stimulation, and bone cartilage regeneration is shown and is generally identified by reference numeral 10. As can be seen, phototherapeutic apparatus 10 includes a brace 12 that is adapted to surround a region of a patient to be treated. In this particular example, the brace includes a body 14 of flexible foam material. A pair of releasable clips 16 engage the ends of the body 14 to keep the brace 12 in a radial configuration. The nature of the foam material allows the brace 12 to conform to the shape of the region to be treated ensuring effective phototherapeutic treatment.

A plurality of interconnected radiation sources 20 is disposed about the interior surface 22 of the brace 12 at different radial locations. Each radiation source 20 includes an array of light sources 24. In this particular example, each radiation source includes an array of nine (9) laser diodes. The laser diodes 24 are driven by power electronics (not shown) and a programmable controller (not shown) allowing the laser diodes 24 to be operated either in a continuous wave (cw) mode or a pulsed mode. A power supply (not shown) carried by the brace 12 provides the necessary operating power.

The nature of the radiation emitted by the laser diodes 24 is selected to ensure penetration of biological tissue and transmission to bone tissues. In this particular embodiment, the laser diodes 24 emit radiation having a wavelength in the range of from about 600 nm to 1300 nm. Typically, the laser diodes 24 emit radiation in the range of from about 600 nm to 900 nm and more particularly, the range of from about 800 nm to 880 nm. In this manner, when the brace 12 is worn by a patient about the area to be treated and the radiation sources 20 are operated, the area to be treated is irradiated with light thereby to assist in bone healing, bone growth stimulation, and bone cartilage regeneration. During operation of the phototherapy apparatus 10, the radiation sources 20 may be illuminated together or in a predetermined sequence independently of one another.

The design of the phototherapy apparatus 10 allows areas of a patient such as the knee, ankle, wrist, arm, elbow, spine, hip, clavicle and neck to be treated. Of course, the phototherapy apparatus 10 may be used to treat other areas or regions of a patient.

Although not shown, the phototherapy apparatus 10 may include a display for displaying information relating to phototherapeutic treatments and/or treatment protocols. hi this manner, visual feedback is provided to the user identifying the manner in which the region being treated is being stimulated using radiation. Sound emitting devices and other visual indicators can be provided to provide audible and visual feedback concerning treatment procedures and/or protocols.

Although the phototherapeutic apparatus 10 is described as including a brace formed of foam material, other configurations are possible. For example, the radiation sources 20 may be embedded inside a deformable gel material, or within a cast to be worn by a patient. Rather than using laser diodes, the radiation sources 20 may alternatively include light emitting diodes, thin-film electroluminescent devices, fiber-optic delivery systems and/or bandages incorporating nanocrystals that emit radiation at predetermined wave lengths in response to excitation from the control hardware and power supply.

Figure 2:
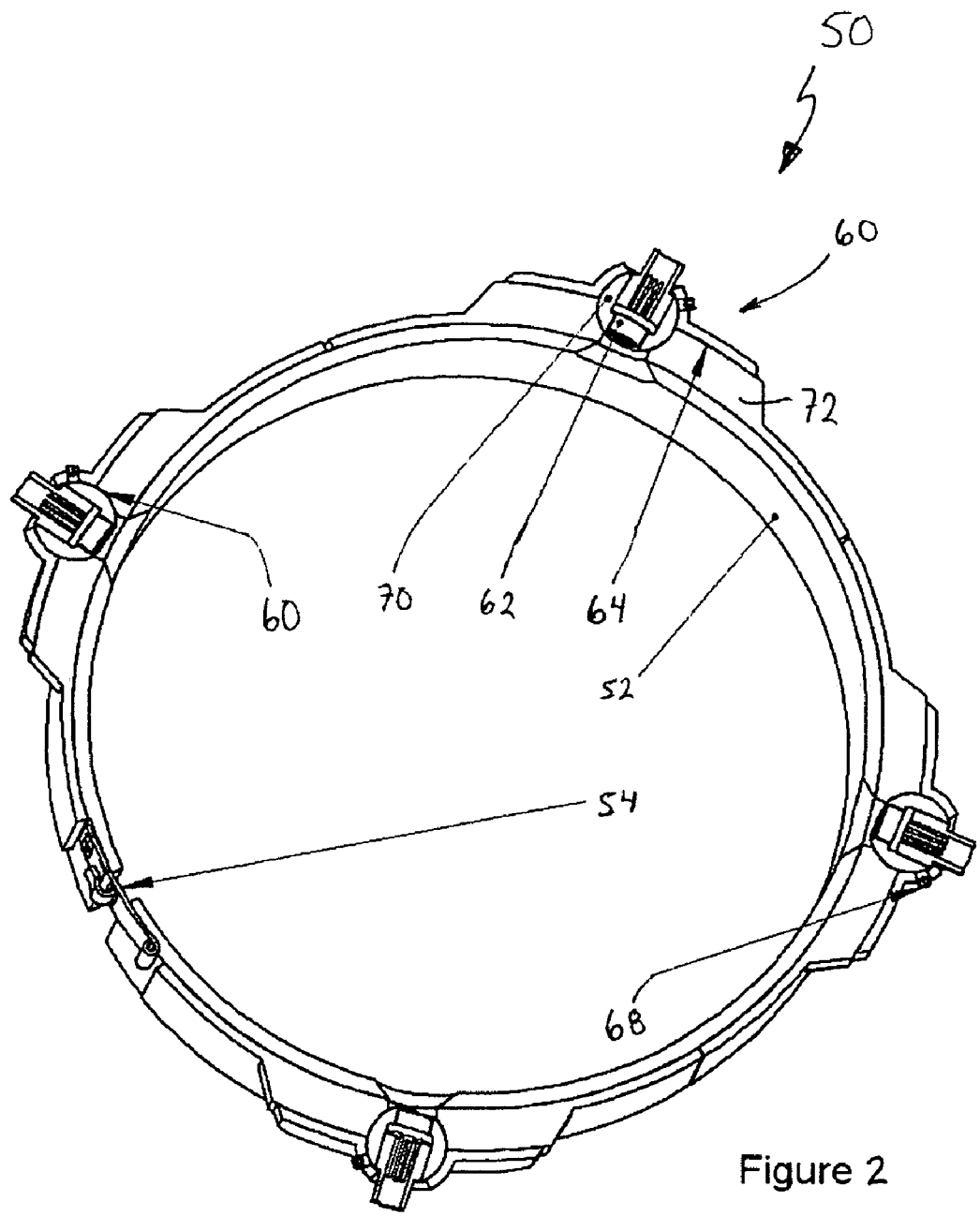
FIG. 2 is a schematic of another embodiment of a phototherapeutic apparatus for bone healing, bone growth stimulation, and bone cartilage regeneration.
Figure 3:
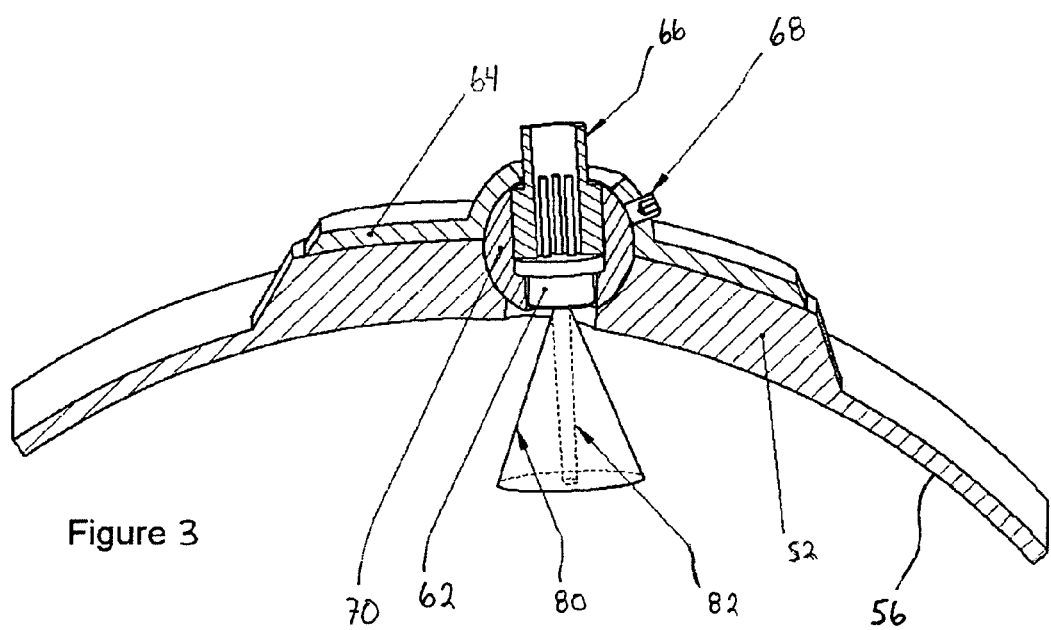
FIG. 3 is an enlarged schematic of a portion of the phototherapeutic apparatus of FIG. 2.

Turning now to FIGS. 2 and 3, another embodiment of a phototherapy apparatus 50 is shown. As can be seen, the phototherapeutic apparatus 50 similarly includes a brace 52 adapted to surround a region of a patient to be treated. A pair of clips 54 engage the free ends of the brace 52 to maintain the brace in a radial configuration. A plurality of radiation sources 60 is disposed about the interior surface 56 of the brace at different radial locations.

In this embodiment, each radiation source 60 includes a single laser diode 62. The position of the laser diode 62 is adjustable to allow radiation emitted by the radiation sources 60 to be accurately directed. In particular, each radiation source includes an upper spherical articulation support 64, a lever 66 facilitating precise alignment and positioning of the laser diode, a lock screw 68 lock the laser diode 62 into position, a spherical articulation 70 supporting the laser diode 62 and a lower spherical articulation support 72. The upper and lower articulation supports 64 and 72 and the spherical articulation 70 form a gimbal-type support for the laser diode 62 thereby to facilitate its orientation.

FIG. 3 better illustrates one of the radiation sources 60 and illustrates traces of an emitted laser ray 80 and a focused laser ray 82.

It can be advantageous to augment the phototherapy radiation with different types of electromagnetic field methods used for promoting healing of nonunion bone fractures, and to provide enhanced bone healing, bone growth stimulation and bone cartilage regeneration.

Although preferred embodiments have been described, those of skill in the art will appreciate that variations and modifications may be made without departing from the spirit and scope thereof as defined by the appended claims.

REFERENCES

Anglen, J. "Enhancement of Fracture Healing With Bone Stimulators", Techniques in Orthopaedics, 17, pp. 506-514, 2002.

De Souza Merli, L. A., Botti Rodrigues Dos Santos, M. T., Genovese, W. J., and Faloppa, F., "Effect of Low-Intensity Laser Irradiation on the Process of Bone Repair", Photomedicine and Laser Surgery, 23, pp. 212-215, 2005.

Karu, T., The Science of Low-Power Laser Therapy, Gordon and Breach Sci. Publ., 1998.

Pinheiro, A. L. B., "Recent studies on bone regeneration", International Congress Series Volume 1248, pp 69-72, 2003; (Lasers in Dentistry: Revolution of Dental Treatment in The New Millennium. Proceedings of the 8th International Congress on Lasers in Dentistry, held in Yokohama, Japan, between 31 July and 2 Aug. 2002).

Trelles M., Mayayo E., "Bone Fracture Consolidates Faster with Low Power Laser", Lasers in Surgery and Medicine, 7, pp. 36-45, 1987.

Tunér, J., and Hode, L., "Low Level Laser Therapy" (Clinical Practice and Scientific Background), Prima Books, (Grangesberg, Sweden, 1999).

Tunér, J., and Hode, L., "The Laser Therapy Handbook", Prima Books, (Grangesberg, Sweden, 2004).

Ueda Y, Shimizu N., "Pulse irradiation of low-power laser stimulates bone nodule formation", Journal of Oral Science 43, pp. 55-60, 2001.

Whelan, H. T. et al., "Effect of Nasa Light-emitting Diode Irradiation on Wound Healing", J. Clin. Laser Med. Surg., vol. 19, pp. 305-314, 2001.

What is claimed is:

1. A phototherapy apparatus comprising:
a body in the shape of a ring into which a region of a patient to be treated is inserted so that said body surrounds said region, said body being formed of material so that said body conforms to the surrounded region; and
a plurality of radiation sources disposed on said body at circumferentially spaced locations, each radiation source including at least one radiation emitting device emitting radiation towards said region, said radiation having a wavelength selected to promote healing, growth stimulation and cartilage regeneration of bone structure within said surrounded region, wherein each radiation source is accommodated by a gimbal-type arrangement about the inner surface of the body allowing the radiation source to be adjusted relative to said body.

2. A phototherapy apparatus according to claim 1 wherein each radiation source includes a plurality of radiation emitting devices.

3. A phototherapy apparatus according to claim 2 wherein said radiation emitting devices are selected from the group consisting of laser diodes, light emitting diodes, thin-film electroluminescent devices, fiber-optic delivery systems, and bandages incorporating nanocrystals that emit radiation at predetermined wavelengths in response to excitation.

4. A phototherapy apparatus according to claim 1 wherein said radiation sources are operated in one of a continuous and pulsed manner.

5. A phototherapy apparatus according to claim 1 wherein said body is formed of foam material.

6. A phototherapy apparatus according to claim 1 further comprising a controller controlling operation of the radiation sources to enable the radiation to be emitted in a desired pattern.

7. A phototherapy apparatus according to claim 6 further comprising a display displaying phototherapy procedures and/or treatment protocols.

8. A phototherapy apparatus according to claim 1 wherein the emitted radiation has a wavelength between ultraviolet and mid-infrared.

9. A phototherapy apparatus according to claim 1 wherein the wavelength of the emitted radiation is in the range of from about 600 nm to 1300 nm.

10. A phototherapy apparatus according to claim 1 wherein the emitted radiation includes visible light, or visible and infrared light, or infrared light.

11. A phototherapy apparatus according to claim 1 wherein the radiation emitted by each radiation source is collimated within a variable solid angle centered on a target area within said region.

12. A phototherapy apparatus according to claim 1 wherein the said phototherapy apparatus is combined with different types of electromagnetic field methods used for promoting healing of nonunion bone fractures.

13. A phototherapy method, comprising:
surrounding said region to be treated with the apparatus of claim 1; and
operating the radiation sources to irradiate the region and bone structure therein with radiation at appropriate wavelengths and power densities for a selected period of time.

14. A phototherapy method according to claim 13, further comprising:
augmenting said radiation generated by said apparatus with different types of electromagnetic field methods used for promoting healing of nonunion bone fractures.

15. A phototherapy apparatus comprising:
a support adapted to overlie and conform generally to a region of a patient to be treated; and
a plurality of radiation sources disposed on said support, each radiation source being accommodated by a gimbal-type arrangement about the inner surface of the body allowing the radiation source to be adjusted relative to said support, each radiation source including at least one radiation emitting device emitting radiation towards said region, said radiation having a wavelength in the range of 800 nm to 880 nm to promote healing, growth stimulation and cartilage regeneration of bone structure within said region.

16. A phototherapy apparatus according to claim 15 wherein each radiation source includes a plurality of radiation emitting devices.

17. A phototherapy apparatus according to claim 16 wherein said radiation emitting devices are selected from the group consisting of laser diodes, light emitting diodes, thin-film electroluminescent devices, fiber-optic delivery systems, and bandages incorporating nanocrystals that emit radiation at predetermined wavelengths in response to excitation.

18. A phototherapy apparatus according to claim 15 wherein said radiation sources are operated in one of a continuous and pulsed manner.

19. A phototherapy apparatus according to claim 15 further comprising a controller controlling operation of the radiation sources to enable the radiation to be emitted in a desired pattern.

20. A phototherapy apparatus according to claim 19 further comprising a display displaying phototherapy procedures and/or treatment protocols.

21. A phototherapy apparatus comprising:
a support adapted to overlie and conform generally to a region of a patient to be treated; and
a plurality of radiation sources disposed on said support at spaced locations, each radiation source emitting radiation towards said region, said radiation having a wavelength selected to promote healing, growth stimulation and cartilage regeneration of bone structure within said region, each radiation source accommodated by a gimbal-type arrangement about the inner surface of the body and being moveable with respect to said support to adjust the direction of radiation emitted thereby.

22. A phototherapy apparatus according to claim 21 wherein each radiation source is lockable to its associated gimbal-type arrangement.

23. A phototherapy apparatus according to claim 21 wherein each radiation source emits radiation having a wavelength in the range of 800 nm to 880 nm.

24. A phototherapy apparatus according to claim 21 wherein said radiation sources are operated in one of a continuous and pulsed manner.

25. A phototherapy apparatus according to claim 21 further comprising a controller controlling operation of the radiation sources to enable the radiation to be emitted in a desired pattern.

26. A phototherapy apparatus according to claim 25 further comprising a display displaying phototherapy procedures and/or treatment protocols.

* * * * *